United States Patent [19]

Neumann et al.

[11] Patent Number: 4,545,218
[45] Date of Patent: Oct. 8, 1985

[54] CRYOGENIC FIXATION APPARATUS

[75] Inventors: Klaus Neumann, Bexbach, Fed. Rep. of Germany; Heinrich Kleber, Vienna, Austria

[73] Assignee: E. Reichert Optische Werke AG, Vienna, Austria

[21] Appl. No.: 651,385

[22] Filed: Sep. 17, 1984

[51] Int. Cl.$^4$ ............................................. F25B 19/00
[52] U.S. Cl. .................................... 62/514 R; 353/54; 356/436; 362/318
[58] Field of Search ............. 62/125, 514 R; 356/436, 356/441, 442; 353/54; 362/318

[56] References Cited

U.S. PATENT DOCUMENTS 1,208,830 12/1916 Pratt ...................................... 356/436
1,565,590 12/1925 Ritterrath ................................ 353/54
3,525,228 8/1970 Anderson ........................... 62/514 R

FOREIGN PATENT DOCUMENTS 210304 5/1909 Fed. Rep. of Germany ........ 353/54

Primary Examiner—Ronald C. Capossela
Attorney, Agent, or Firm—Alan H. Spencer; Stephen Raines

[57] ABSTRACT

Cryogenic-fixation apparatus comprises a light source, a beam from which enter cooling liquid in a bath, through a window in the underside of the bath. The beam can be directed upwardly by means of a reflecting prism. When a lid of the bath is closed, the beam leaves the space defined by the path through an exit port in the lid, and is incident upon a specimen mounted on a specimen holder located above the exit port, the specimen holder being secured to an injector rod.

6 Claims, 3 Drawing Figures

CRYOGENIC FIXATION APPARATUS

BACKGROUND OF THE INVENTION

This invention relates to cryogenic-fixation apparatus.

DESCRIPTION OF THE PRIOR ART

Prior to the cryogenic-fixation of a small specimen, the small specimen, which may be a small drop of a suspension or a thin layer of a tissue culture, is applied to a specimen holder. Manipulating the specimen onto a holder, and also, in certain circumstances, connecting micro-electrodes to the holder, or modifying the holder in other ways, are important steps in successfully accomplishing a cryogenic-fixation operation. Accordingly, a stereoscopic microscope is commonly used when preparing the specimen for cryogenic-fixation. Following a cryogenic-fixation operation, the specimen is removed carefully from the cooling bath, which operation also requires care.

Since the preparation and post-cryogenic-fixation operations call for careful manipulation of the specimen holder, these operations require good illumination of the specimen holder and the cooling bath. The cooling bath, commonly comprises a metal vessel, defining a cylindrical chamber for the cooling liquid, the chamber typically measuring approximately 20 mm in diameter and 100 mm in height. The temperature of the cooling liquid in the bath is thermostatically controlled. Since the specimen-preparation procedure requires the use of both hands and the space is also required for the injection system, the stereoscopic microscope, and the cryogen supply line, installing an arrangement which is capable of providing the necessary illumination presents difficulties. It is particularly difficult to combine illumination of the specimen holder with overall illumination of the cooling bath.

OBJECTS OF THE INVENTION

It is an object of the invention to provide an arrangement which both illuminates the specimen holder and provides overall illumination of the interior of the cooling bath, in a manner which is both simple and generally applicable to cryogenic-fixation apparatus.

BRIEF DESCRIPTION OF THE INVENTION

According to the invention there is provided cryogenic-fixation apparatus comprising a cooling bath for a cooling liquid, a window on an underside of said bath, and a light source for directing a beam of light upwardly through the window to illuminate the interior of the cooling bath.

When the apparatus is in use, the light beam enters the cooling bath from below, through the window which is made of glass, or of another cold-resistant and cryogen-resistant material, and which is sealed in the underside of the cooling bath. A specimen holder is normally located above the cooling bath and the light beam, rather than being directed to illuminate the whole interior of the bath, is directed towards the specimen holder and a specimen on the holder. Thus one light source only is required. The specimen holder can be viewed under a microscope when mounting a specimen on the holder, the apparatus imposing no restriction on a two-handed manipulation of the specimen holder and specimen.

In one embodiment of the invention, the light source is disposed directly below the cooling bath. A heat-barrier filter may be provided to filter out the ultrared component of the light beam before the beam enters the cooling bath. The heat-barrier filter may be comprised by the window.

In an alternative embodiment of the invention, the light source is disposed to one side of the cooling bath, and wherein the apparatus further comprises a reflecting means for directing the beam of light upwardly through the window. This arrangement facilitates replacement of the light bulb. The reflecting means may comprise, for example, a prism, a mirror, or a light guide. Advantageously the light source comprises a reflector lamp which emits light with a weak ultrared component, or alternatively a fibre-optic light guide may be provided, of a kind which eliminates the greater part of the ultrared component from a beam.

The cooling bath may comprise a lid with a port for the transmission of the beam of light which has traversed the cooling bath. The port enables the cooling bath to be inspected and a specimen-preparation operation to be carried out on the specimen holder whilst the cooling bath is covered.

DETAILED DESCRIPTION OF THE DRAWINGS

Illustrative embodiments of the invention are described in detail by reference to the accompanying drawings, wherein.

DETAILED DESCRIPTION OF THE INVENTION

Figure 1:
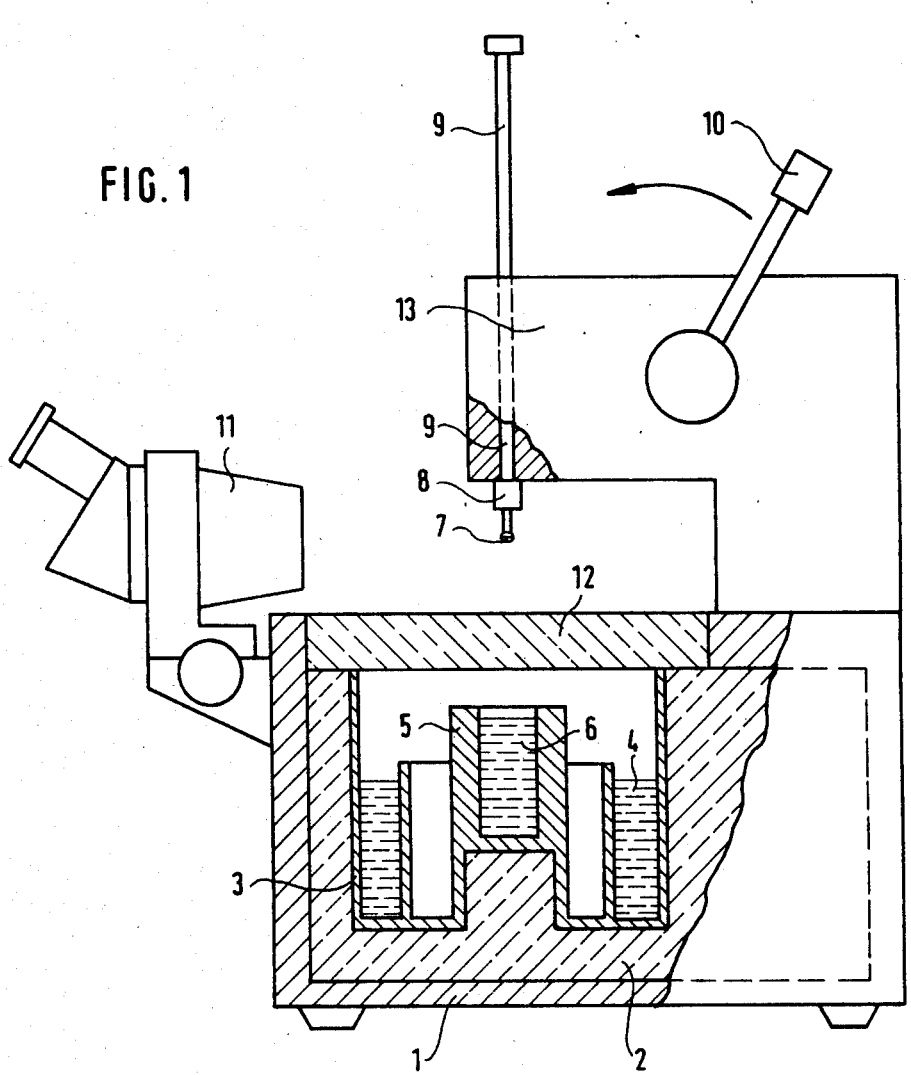
FIG. 1 is a diagrammatic cross-sectional side view of a known arrangement of cryogenic-fixation apparatus.

FIG. 1 illustrates a known form of cryogenic-fixation apparatus. A pot-shaped vessel 3 containing a cryogenic liquid in the form of nitrogen 4 is surrounded by insulation 2 in a housing 1. The liquid nitrogen 4 cools a bath in the form of a metal cylindrical body 5 directly, or indirectly when in a standby operating mode as illustrated. The body contains a cooling medium 6 into which a specimen 7 is immersed for cryogenic-fixation. The temperature of the cooling medium is maintained by thermostatic means.

The specimen 7 is mounted on a specimen holder 8 which, in turn, is mounted on an injector rod 9 on a support 13. The injector rod can be lowered into the cooling liquid 6, upon operation of a lever 10. A stereoscopic microscope 11 is used to observe the mounting of the specimen 7 on the specimen holder 8, this operation frequently being extremely difficult. During the specimen-mounting operation, whilst the apparatus is in a standby operating mode, a thermally insulating lid of the vessel 3 which contains the cooling bath 5, is maintained in a closed position to limit consumption of nitrogen and to prevent damaging precooling of the specimen 7 on its holding device 8.

In this known arrangement, the mounting of the specimen is carried out with insufficient illumination. The stereoscopic microscope 11 occupies that side of the arrangement which faces the user, whilst the opposite, rear side is occupied by the support 13. Since, preparing, the specimen generally requires the use of both hands, the other two sides are also eliminated for the installation of a light source. Following immersion of the specimen 7 in the cooling bath 5, the specimen can be seen and handled only with difficulty in the cylindrical space defined by the bath containing the cooling liquid 6.

Figure 2:
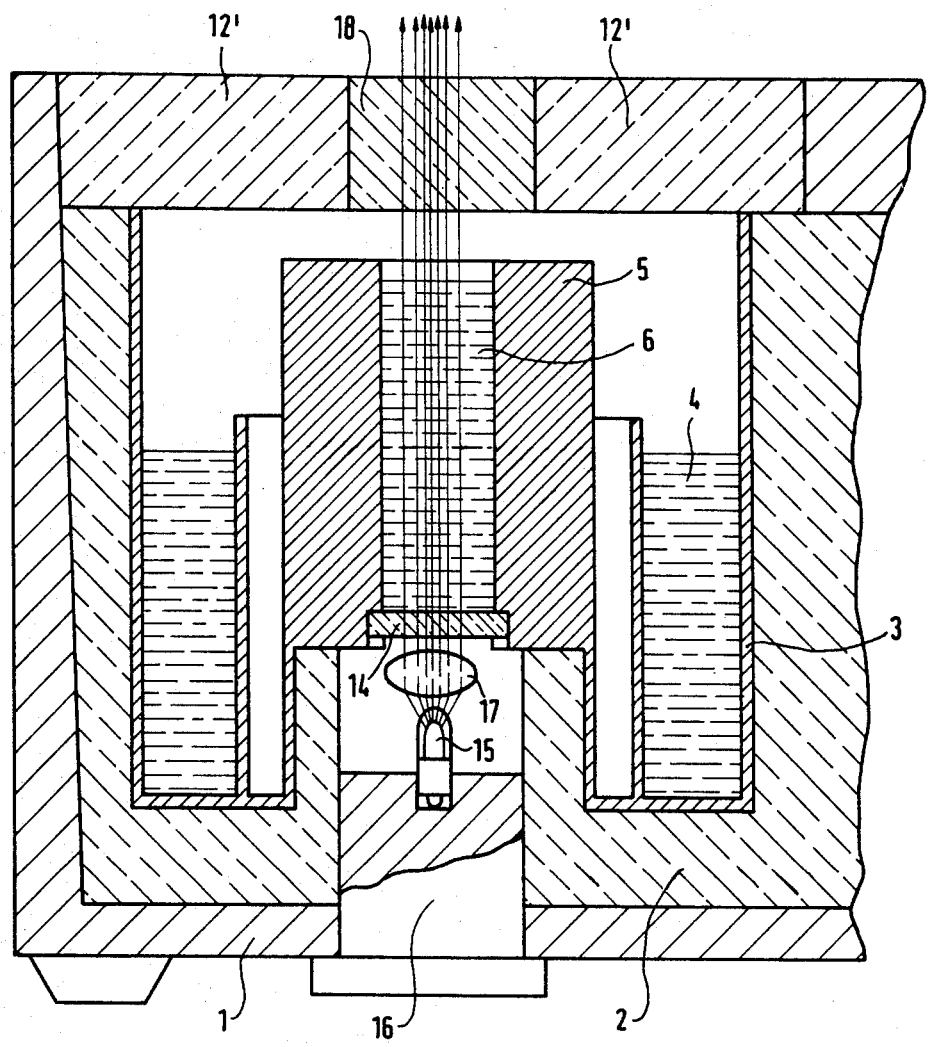
FIG. 2 is a diagrammatic cross-section of one embodiment of the apparatus in accordance with the invention, with a light source which is located immediately below a cooling bath.

In the arrangement of apparatus shown in FIG. 2 a glass window 14 forms the bottom of the cooling bath 5 containing the cooling liquid 6, the cooling bath, and the injection system being the same as the arrangement shown in FIG. 1 in other respects. A light source in the form of a high-output quartz-iodine lamp 15 is located immediately below the cooling liquid 6. The lamp is mounted in a holder 16 which, after tilting the appliance, can be removed, thereby enabling the light bulb to be changed without difficulty. A collector lens 17 focusses rays from the lamp. A heat-barrier filter is provided for filtering out or absorbing the ultrared component of light from the lamp, the filter being provided by window 14 or by a reflector of the lamp. The window is cooled by the cooling liquid 6.

Figure 3:
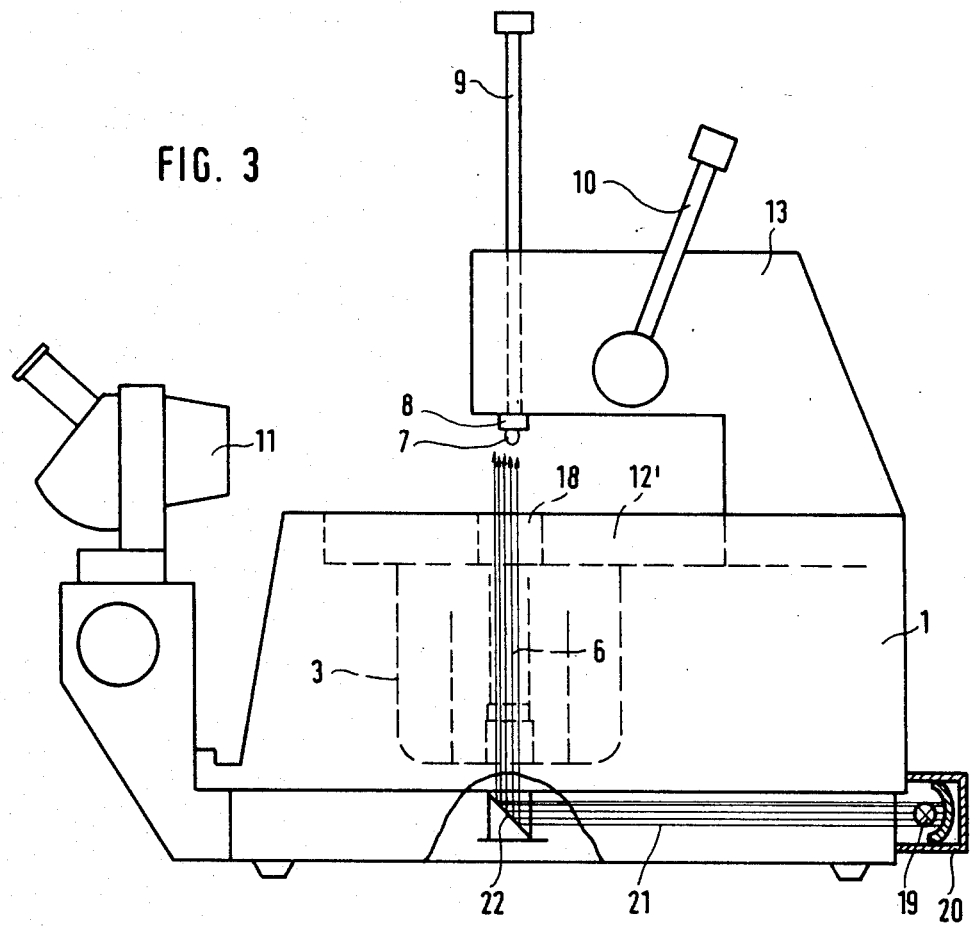
FIG. 3 is a diagrammatic cross-section of a further embodiment of apparatus in accordance with the invention.

In the embodiment of apparatus shown in FIG. 3, a part in the form of transparent insert 18 in lid 12' permits a beam of light to pass out of the cooling bath, so that the specimen holder 7 can be illuminated when the lid is closed.

A reflector lamp 19 is mounted externally of the apparatus, in a holder 20 mounted on a rear wall. The holder can, alternatively, be mounted on one of the two side walls. The beam 21 emitted by the reflector lamp is directed by a reflecting means in the form of a prism 22 upwardly into the chamber defined by the cooling bath.

Various modifications can be made to the apparatus shown in FIGS. 2 and 3. For example, various optical elements can be introduced into the optical path between the light source and the specimen holder and, in particular, the reflecting means can comprise alternatives to a prism such as a mirror or a light guide such as a fibre-optic light guide. Various forms of light source can be used. The port which enables the light to emerge from the cooling bath can be a solid transparent body, a tube with two transparent cover plates, a lens for further focussing of the rays, or a heat-absorbing glass.

We claim:

1. Cryogenic-fixation apparatus comprising a container for a cooling liquid means to cool said container, a window in the underside of said container, a light source and optical means for directing a beam of light upwardly through said window to illuminate the interior of the cooling bath.

2. Apparatus according to claim 1, wherein the light source is disposed directly below the container.

3. Apparatus according to claim 1, wherein the light source is disposed to one side of the container, and wherein the optical means includes a reflector for directing the beam of light upwardly through the window.

4. Apparatus according to claim 1, wherein the optical means comprises a fibre-optic light guide.

5. Apparatus according to claim 1, wherein the light source includes a reflector, and said reflector absorbs at least a portion of the infrared component of light.

6. Apparatus according to claim 1 in which a lid for the cooling bath is provided with a port for the transmission of the beam of light which has traversed the said container.

* * * * *